(12) United States Patent
DePetrillo

(10) Patent No.: US 7,866,321 B2
(45) Date of Patent: Jan. 11, 2011

(54) REUSABLE RESTRAINING APPARATUS WITH DOUBLE LOCK

(76) Inventor: Paul R. DePetrillo, 73 Wheeler Ave., Cranston, RI (US) 02905

( * ) Notice: Subject to any disclaimer, the term of this patent is extended or adjusted under 35 U.S.C. 154(b) by 207 days.

(21) Appl. No.: 11/668,302

(22) Filed: Jan. 29, 2007

(65) Prior Publication Data

US 2007/0180870 A1 Aug. 9, 2007

Related U.S. Application Data

(60) Provisional application No. 60/743,206, filed on Feb. 1, 2006.

(51) Int. Cl.
*A61F 5/37* (2006.01)
*B65D 63/00* (2006.01)
*E05B 73/00* (2006.01)

(52) U.S. Cl. .......................... 128/878; 24/16 PB; 70/15

(58) Field of Classification Search ............... 24/16 PB, 24/17 A, 17 B, 70 R, 70 ST; 297/250; 128/869, 128/878; 70/16, 15, 17, 58, 18
See application file for complete search history.

(56) References Cited

U.S. PATENT DOCUMENTS

| 372,510 | A | * | 11/1887 | Bean | 70/16 |
| 3,146,614 | A | * | 9/1964 | Von Frantzius | 70/16 |
| 5,377,510 | A | * | 1/1995 | Smith | 70/16 |
| 6,101,682 | A | * | 8/2000 | Parsons | 24/16 PB |

* cited by examiner

*Primary Examiner*—Patricia M Bianco
*Assistant Examiner*—Tarla R Patel
(74) *Attorney, Agent, or Firm*—Barlow, Josephs & Holmes, Ltd.

(57) ABSTRACT

The restraining apparatus includes a housing having an interior. A first end of a binding loop strap is attached to the interior of the housing and a second end is routed through the housing and connected to a handle for pulling with one hand. The binding loop is slideably movable in a first direction to reduce the overall dimension of the loop. The binding loop is slideably movable in a second direction to expand the overall dimension of the binding loop. A locking mechanism is disposed in the interior of the housing and connects to the binding loop. The locking mechanism includes both a lower cleat and an upper cleat for controlling the movement of the binding loop through a groove within the locking mechanism. When the lower cleat is engaged, the overall dimension of the binding loop decreases. When the upper cleat is engaged, the overall dimension of the binding loop increases.

6 Claims, 7 Drawing Sheets

REUSABLE RESTRAINING APPARATUS WITH DOUBLE LOCK

CROSS REFERENCE TO RELATED APPLICATION

This application is related to and claims priority from earlier filed provisional patent application Ser. No. 60/743,206, filed Feb. 1, 2006.

BACKGROUND OF THE INVENTION

The present invention relates to restraining apparatus, namely restraining apparatus used to secure any part of the body, such as the hands, wrists and legs of a person. More generally, the present invention relates to a device that releasably locks to an object for control thereof.

In the prior art, restraining apparatus, such as hand cuffs, are well known devices for securing the hands (or ankles, legs) of a person together. There is a well-known problem with conventional hand cuffs in that the person using them must use both hands to operate the cuffs. In a police scenario, for example, requiring the user, such as a policeman, to use both hands which is very dangerous in that the policeman must typically first holster their weapon before attempting to install the handcuffs on the person to be detained. Known hand cuffs have the severe disadvantage of requiring two hands for operation and two distinct steps of installation where each side of the cuff is installed separately.

There have been attempts in the prior art to provide such a restraining apparatus that can solve the problems above. However, these devices are awkward and difficult to use. In particular, these prior art restraint systems do not adequately control the device itself. More specifically, many of these restraining apparatus include a length of binding loop or strap material with tooth structure thereon to serve as the structure to encircle the object to be restrained. This binding loop, in the prior art, is controlled by some type of ratcheting structure so the overall length can be set. Typically, this is a one way locking characteristic where the binding loop is routed through the ratcheting structure to form a loop. This ratcheting structure only permits control of the strap in one direction, namely, in the locking direction where the size of the loop of material can be only made smaller and smaller. This is particularly problematic if the loop is made too small because a loop that is too small can injure the person on which the restraining apparatus is installed. Thus, if the loop is too small, e.g. constricting the user's wrists, the entire device must be completely cut off from the user and a new device must be installed with more careful attention not to encircle the wrists too tightly.

Similarly, when a restraining apparatus is attached to someone and it is not longer desired to have the restraint on the person, the restraining apparatus must be completely cut off of the person. Thus, prior art devices are disposable in nature. Since prior art devices are disposable, for cost reasons, they are made of lighter weight materials and not made as ruggedly as desired.

Therefore, there is a particular need in the industry to provide a restraint system that can be quickly and easily installed on a person to be detained, such as a prisoner. Further, one handed operation is also highly desired to obviate the need for the policeman to have to holster his or her weapon to operate and manipulate the cuffs. Also, there is a need for a restraining apparatus that is reusable to save cost on disposable prior art devices and provide a higher quality device. There is also a particular need in the art to better control the ratchet binding loops, namely, to control movement of the binding loops in both the tightening direction as well as the loosening direction. Thus, there is a need for a double locking and reusable restraining apparatus.

SUMMARY OF THE INVENTION

The present invention preserves the advantages of prior art restraining apparatus. In addition, it provides new advantages not found in currently available handcuffs or restraining apparatus and overcomes many disadvantages of such currently available apparatus.

The invention is generally directed to the novel and unique restraining apparatus that provides a reusable, adjustable, and easy-to-use restraint. A restraining apparatus is used to secure objects such as persons, animals, and other types of objects. The present invention provides for a restraining apparatus that can be used multiple times without having to be cut or destroyed. In order to deploy the restraining apparatus, the present invention provides for a user to easily deploy the device with minimal user intervention. For example, the restraining apparatus may be deployed using one hand. In addition, the restraining apparatus may be adjusted for the tightening or loosening of the restraints using a locking mechanism.

The restraining apparatus has many advantages over prior art restraining apparatus. The restraining apparatus includes a rigid housing having an interior. The rigid housing is made of durable materials suitable for more than use. A proximal end of a binding loop is attached to the interior of the housing and a distal end is connected to a handle for pulling with one hand. The binding loop has sufficient length such that the distal end is insertable through the housing thereby to form a binding loop of adjustable dimension. The binding loop is slideably movable in a first direction to reduce the overall dimension of the loop. The binding loop is slideably movable in a second direction to expand the dimension of the binding loop.

A locking mechanism is disposed in the interior of the housing and connects to the binding loop. The locking mechanism includes a groove for insertion of the binding loop. The locking mechanism includes both a lower cleat and an upper cleat for controlling the movement of the binding loop through the groove. The lower cleat is pivotally mounted to the interior of the locking mechanism and is designed for engaging the binding loop to control movement. The lower carriage encloses the cleat and controls the movement of the lower cleat that engages the binding loop. An upper cleat is pivotally mounted to the interior of the locking mechanism and is designed for engaging the binding loop to control movement. An upper carriage for controlling the movement of the upper cleat encloses the upper cleat for that engages the binding loop. When the lower cleat is engaged to the binding loop within the groove, the overall dimension of the binding loop decreases when the binding loop moves in the first direction. When the upper cleat is engaged to the binding loop within the groove, the overall dimension of the binding loop increases when the binding loop moves in the second direction.

It is therefore an object of the present invention to provide an improved restraining apparatus that can be deployed by a user using only one hand.

It is an object of the present invention to provide an improved restraining apparatus that has a handle that facilitates easy deployment by a user.

It is a further object of the present invention to provide an improved restraining apparatus that is suitable for multiple uses or reusable.

Another object of the present invention to provide an improved restraining apparatus that has a locking mechanism that allow for either tightening or loosening of the binding of the restraining apparatus.

A further object of the present invention is to provide an improved restraining apparatus that has a locking mechanism that is double-locking.

Another object of the present invention is to provide an improved restraining apparatus that has a locking mechanism with sufficient strength to withstand more than one use.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE PREFERRED EMBODIMENT

Figure 1:
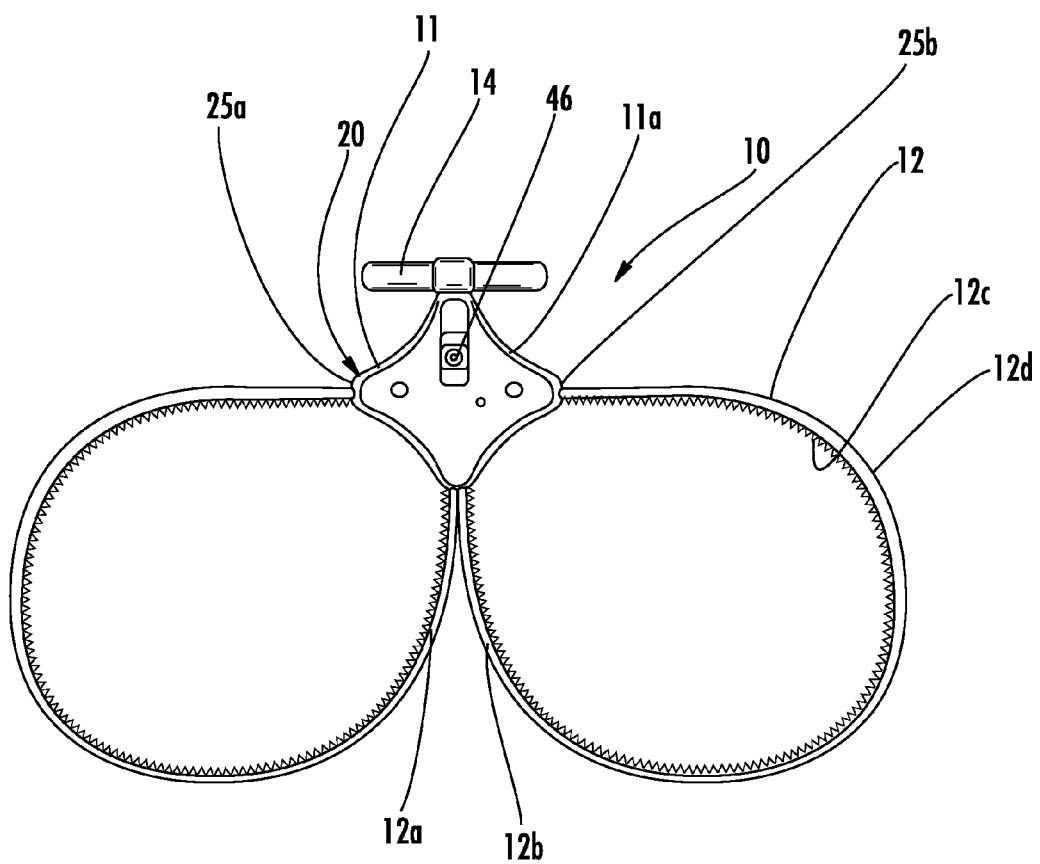
FIG. 1 is a top view of the restraining apparatus of the present invention.

Turning first to FIG. 1, a restraining apparatus 10 for restraining an object, in accordance with the present invention, is shown. The apparatus includes a rigid outer housing 11 that can be a pair of mating shells, for example, to surround the interior components, which will be discussed in detail below. The housing 11 may be made of rigid and rugged materials to allow the restraining apparatus 10 more than one use or deployment. The housing 11 may be milled or molded from metal alloy or high impact composite material. In one embodiment, the housing 11 may consist of a material such as aluminum or composite ABS.

The housing 11 has an ergonomic shape that assists in the deployment of the restraining apparatus 10 with minimal effort by a user. Preferably, the ergonomic shape of the housing 11 may assist a user in deployment of the restraining apparatus 10 with one hand. The curved edges 11a are easily gripping by the user's fingers. More particularly, the deployment of the restraining apparatus 10 may be done with one hand by the user while holding a weapon or detaining a suspect. In one embodiment, the ergonomic shape of the housing 11 may include a rectangular shape or any other shape that is desired.

Still referring to FIG. 1, a binding loop of strap material 12, with ratchet teeth thereon, is provided may have a proximal end that anchors within the housing 11 at locations 25a, 25b on opposing sides of the housing 11. The free ends 12a, 12b of the loop 12 are routed through the housing 11 to connect to handle 14. Details of the control of the routing of the loop of material 12 through the housing will be discussed in detail below. The binding material 12, formed in two loops for restraining two objects, such as arms or legs, at the same time, is preferred. The strap material 12 preferably consists of rugged material suitable for multiple uses or reuse. The rugged material may consist of UV, high impact, protected composite material, which remains pliable and able to withstand great pressures.

The binding loop of strap material 12 has sufficient length such that the distal end is insertable through the housing 11 thereby to form a binding loop 12 of adjustable dimension. The overall lengths of the binding loop 12 are determined by the user, as any length may be used. For example, a 18" binding loop is recommended for wrists, and a 22" binding loop is recommended for foot or leg restraint.

The binding loop strap material 12 has a first surface 12c containing a tooth structure suitable for ratcheting movement. A second surface 12d is located opposite the first surface and bounded to the first surface. Both the first and second surfaces 12c, 12d are preferably formed to facilitate slideable engagement through the interior of the housing 11. In one embodiment, the binding loop may have a tooth structure with a tooth that is 0.050" pitch, 0.025" high, 60° angle, and 0.340" wide but any type of tooth or ratcheting structure may be used to suit the application at hand.

In one embodiment, one or more binding loops 12 may connect to the housing 11. The additional binding 12 may be in various shapes or sizes depending upon the intended use of the restraining apparatus. In addition, the binding loop 12 may be side or side or mounted upon each other for use in a variety of configurations.

Still referring to FIG. 1, a handle 13 is attached to the distal end 12a of the binding loop strap material 12 to enable a user to deploy the restraining apparatus 10 with one hand. The handle 13 may consist of rugged materials suitable for multiple uses. The rugged materials may include a solid aluminum hardened to the surface consistency of stainless steel. The handle 13 may also incorporate a threaded steel shank through its center (not shown), for strength, and an ergonomically shaped handle grip portion for maximum grip. In addition, the handle 13 may be dispersed with a rubber coating to aid in grippage, or it may be molded from high impact plastic for an ABS (composite) version.

In one embodiment, the handle 13 contains a steel eyelet (not shown) for securing in the center. This eyelet may be secured to a stationary object, such as a locking hasp mounted on or inside a law enforcement vehicle, to facilitate the incarceration (lock-down) of a suspect or prisoner. As a result, the steel eyelet on the handle 13 gives the law enforcement official the advantage of incarcerating the restrained prisoner when out-numbered.

Figure 2:
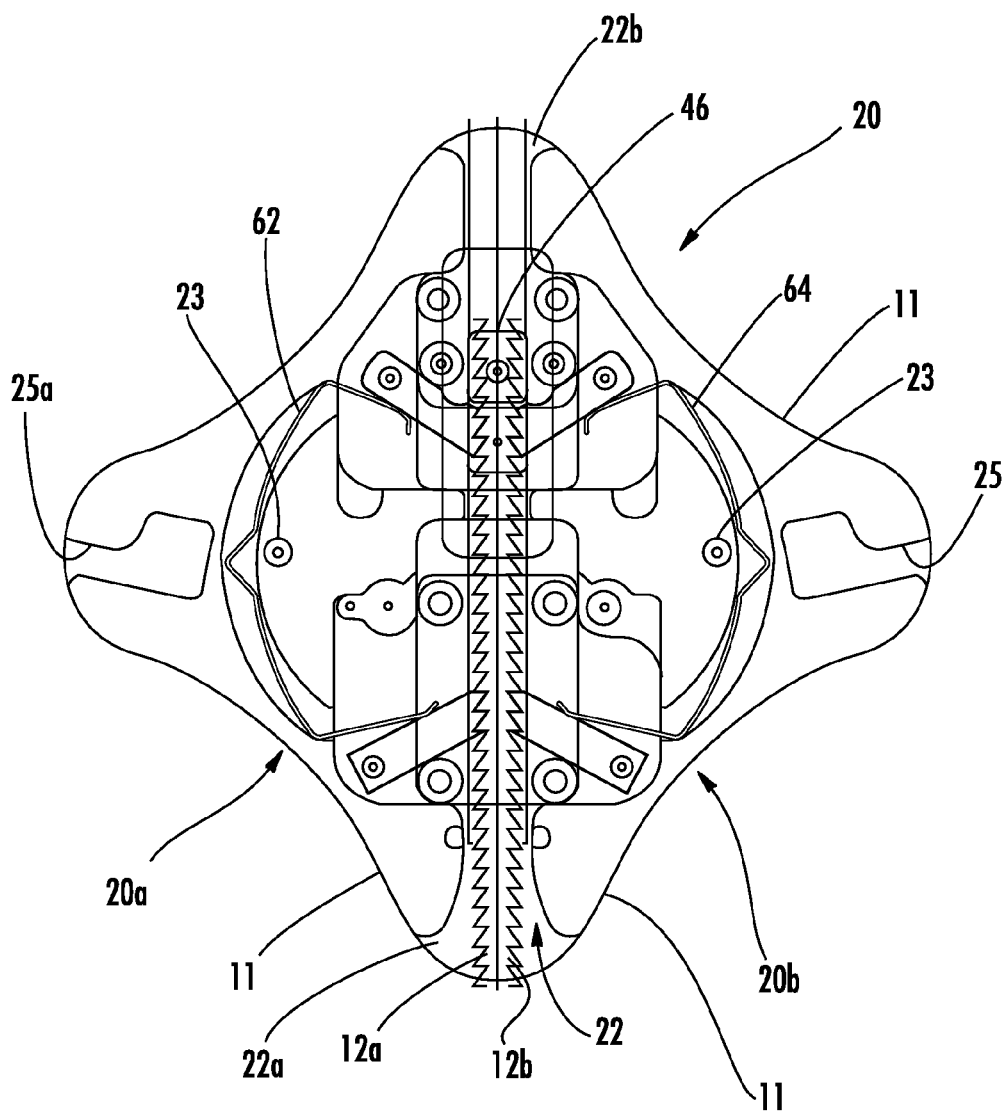
FIG. 2 is a cross-sectional view through the locking mechanism of the restraining device of the present invention.

Now turning to FIGS. 2-8, details of the locking mechanism 20 of the present invention is shown. The locking mechanism 20 is disposed in the interior of the housing 21. FIG. 2 shows the top of outer housing 11 removed for illustration purposes to reveal the locking mechanism 20 therein. The locking mechanism 20 is preferably made of two sides 20a, 20b that are positioned apart from one another to form a channel or groove 22 that is further define by the housing 11. The fastener holes 23, on opposite sides of each half of the locking mechanism 20, may accept a screw to hold a separable cover portion of housing 11 in place.

The locking mechanism 20 is manufactured to allow for insertion of the binding loop free ends 12a, 12b of strap material 12 into groove 22, while the opposing ends are respectively anchored at binding anchor points 25a and 25b. The strap material, generally referred to as 12, controllably moves in either upwardly in a first direction or downwardly in a second direction. In one embodiment, the first direction may be movement of the strap material 12 from the bottom of the groove 22 at 22a to the top of the groove 22b, while moving the binding loop 12 through the groove 22. Likewise, the movement in the second direction may be movement of the binding loop 12 from the top of the groove 22b to the bottom of the groove 22a, while moving the binding loop strap material 12 through the groove 22. To prevent tampering with the movement of the binding loop 24, small security holes or apertures are may be located within the groove 22 which contain pins to block any attempts at infiltrating the locking mechanism 20.

The present invention is unique it that the movement of the strap material, and therefore the sizing and tightness of the loops formed, can be controlled with ease and to a high degree of precision. As will be discussed below, a unique cleat and carriage system is employed to carry out the invention.

Figure 3:
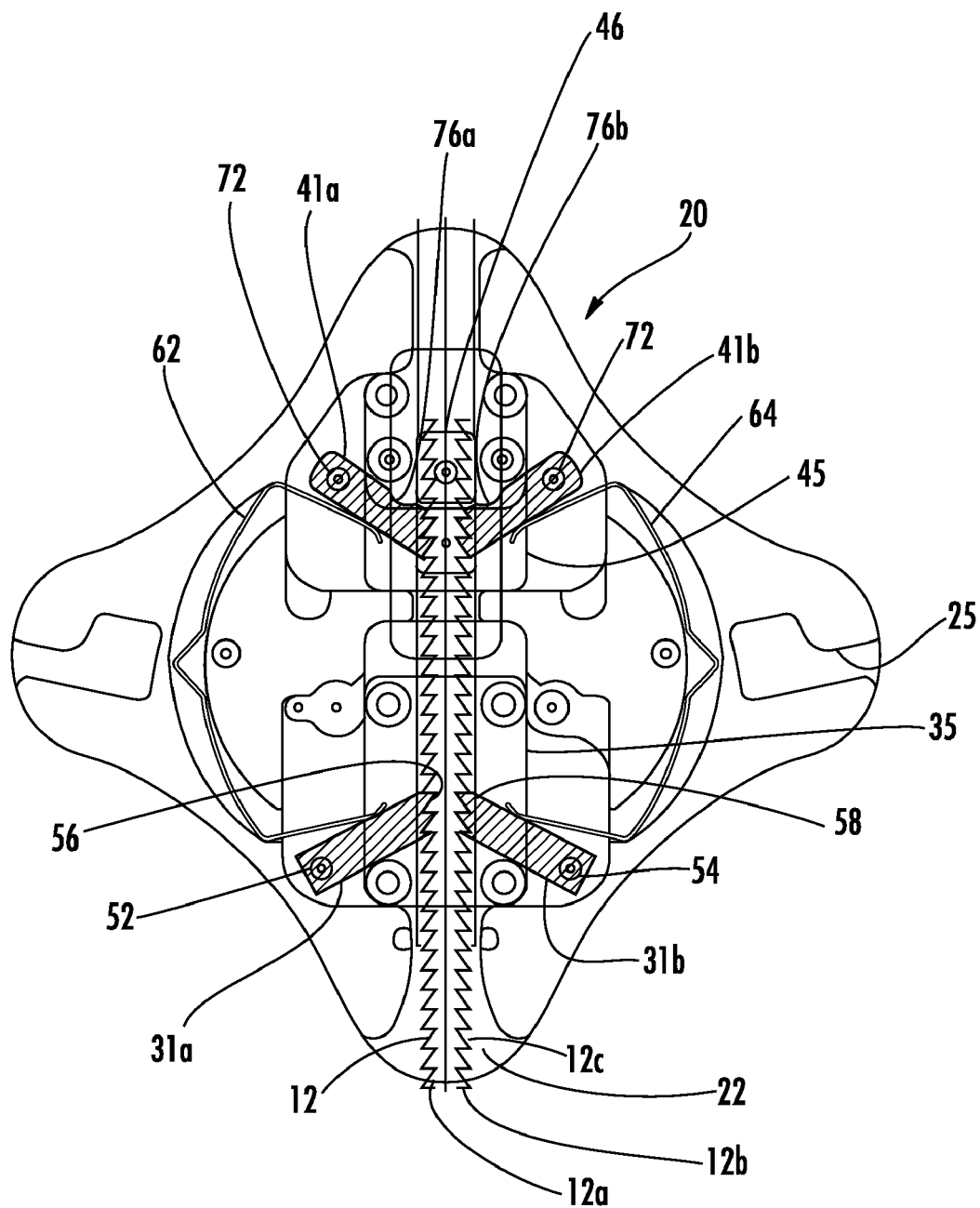
FIG. 3 is a cross-sectional view through the locking mechanism of FIG. 2 with cleats highlighted.

Now turning to FIGS. 2 and 3, which shows the cleats in highlight, a further details of the locking mechanism 20 is shown. The locking mechanism 20 consists of lower cleats 31a and 31b for controlling the movement of the binding loop strap material 12 through the groove 22. The lower cleats 31a, 31b are pivotally mounted to the locking mechanism 20 at pivot points 52 and 54, respectively. The respective free ends 56, 58 of the cleats 31a and 31b, engage with the tooth structure side 12c of the binding loop straps 12a and 12b. The lower cleats 31a and 31b engage the tooth structure of the binding loop 32 to ratchet the movement of the binding loop 12 in the first direction. The ratchet engagement of the lower cleat 31 permits the binding loop 32 to tighten until a dimension of the binding loop 32 is reached by the user. In FIG. 3, this tightening corresponds to movement of the straps 12 in an upward direction, as a result of pulling the handle 13 upwardly.

It should be understood that the lower cleats 31a, 31b may contain various configurations. For instance, the lower cleats 31a, 31b may employ more than one lower cleat to control the movement of the binding straps 12 for a stronger ratcheting mechanism. In addition, the lower cleats 31a, 31b may contain a tooth structure or other surfaces, such as an abrasive or non-smooth surface, for engaging the binding loop 32.

Figure 4:
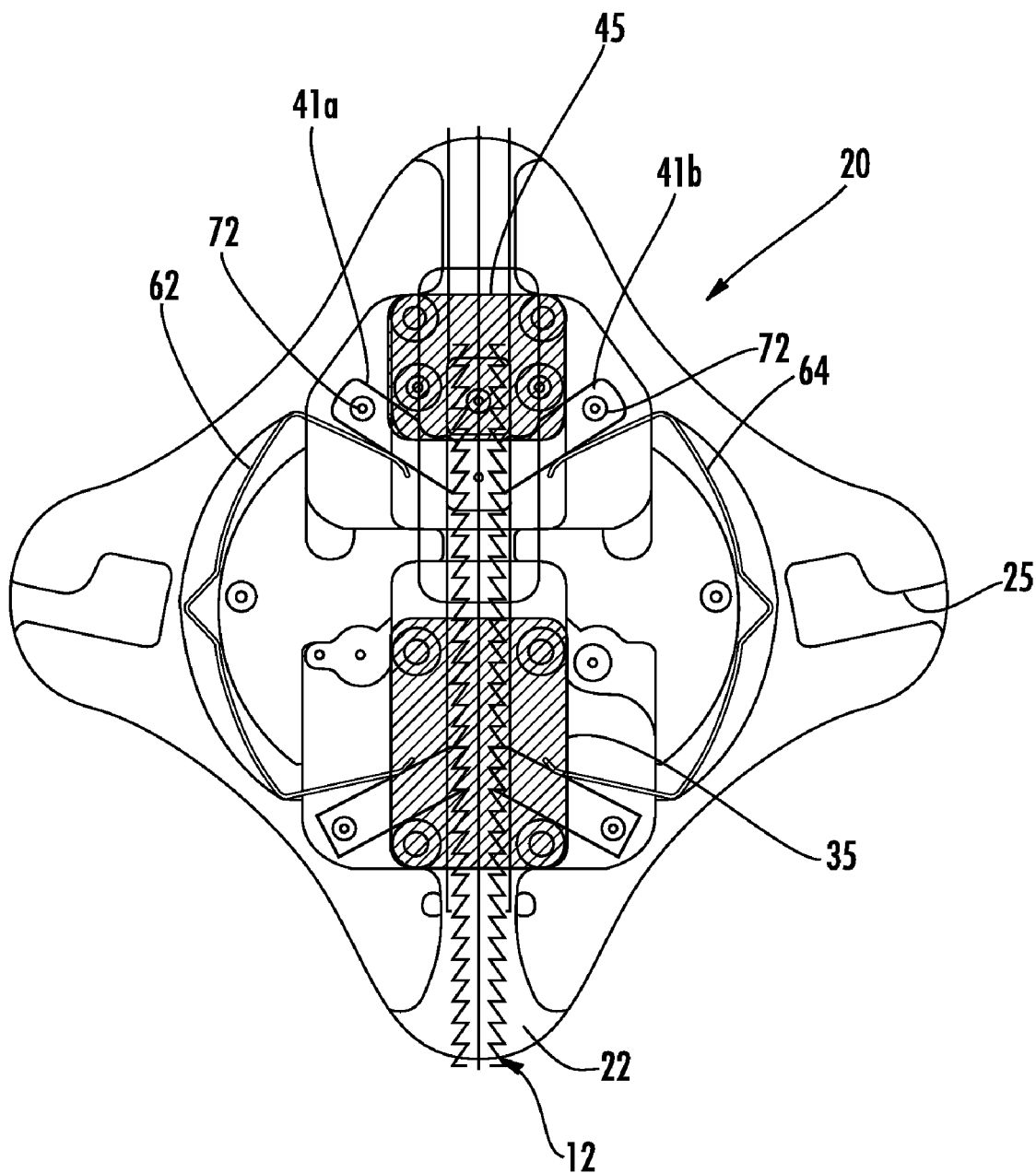
FIG. 4 is a cross-sectional view through the locking mechanism of FIG. 2 with carriages highlighted.
Figure 7:
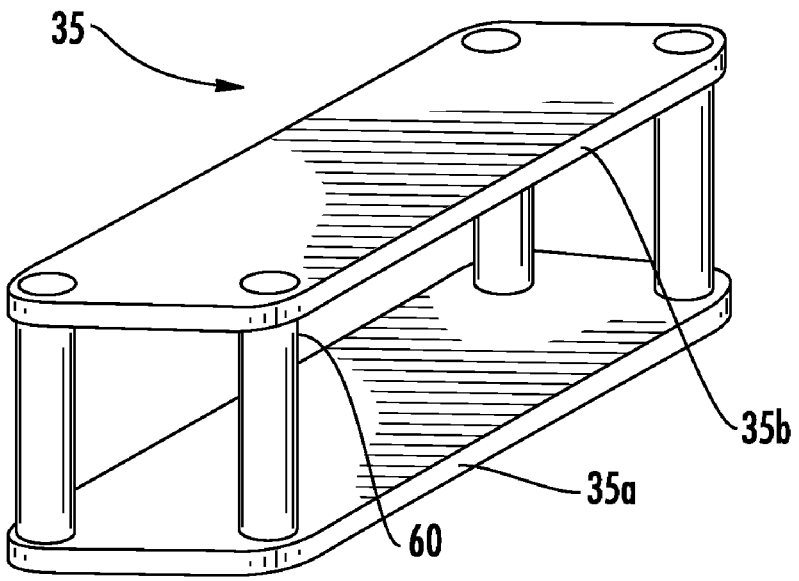
FIG. 7 is a perspective view of the lower carriage.

A lower carriage 35 is also provided for slideable adjustment and control of the movement of the lower cleats 31a, 31b. FIG. 4 highlights the carriages, including the lower carriage 35. FIG. 7 further illustrates a perspective view of the lower carriage. The lower carriage 35 has two or more plates 35a, 35b, preferably made of metal, with four posts 60 in each of the corners to provide a structure for receiving the lower cleats 31a, 31b. The lower carriage 35 is spring-biased in a downward direction to ensure that the cleats engage the straps 12. A wire springs 62 and 64, namely the may be used for this purpose but any type of spring may be employed. When the lower carriage 35 is moved upwardly towards the top of the groove 22b and into a set position, and may decrease the sizes of the loops formed by the straps 12. The cleats 31a, 31b automatically lift up off the teeth 12c when the handle 13 is pulled in view of the direction of the teeth 12c. When the lower carriage 35 is at its lowermost point, the loops of strap material 12 are prevented from getting any larger.

Alternatively, a lower carriage 35 may contain various configurations. For instance, the lower carriage 35 may employ more than or less than two plates 35a, 35b to receive the lower cleats 31a, 31b. In addition, the lower carriage 35 may employ more than or less than four posts 60 to secure the plates 35a, 35b. Also, the lower carriage 35 may slide in a variety of directions including horizontal or vertical slideable adjustment.

Figure 5:
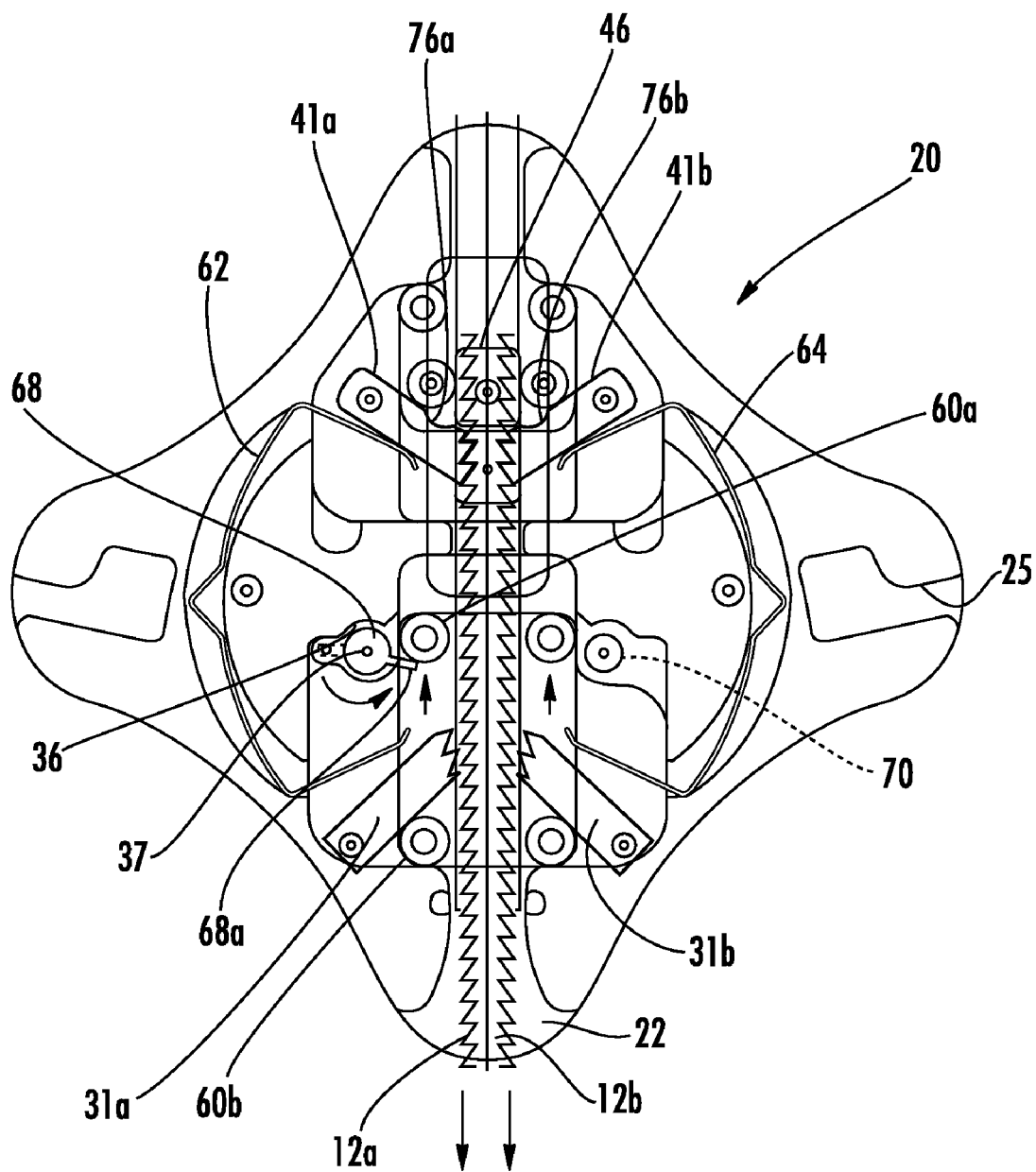
FIG. 5 is a cross-sectional view through the locking mechanism of FIG. 2 with key engaged to permit loosening of the strap.

For added control, as best seen in FIG. 5, the lower carriage 35 may contain an aperture or keyhole 36, to receive a barrel of a key. In one embodiment, the keyhole 36 may receive a standard cuff key 68. The keyhole 36 includes a key pin 37. The flange portion 68a of a key 68 engages with a post 60 of the lower carriage 35 for upward movement of the lower carriage 35. The keyhole 36 being positioned such that the insertion of the key 68 into the keyhole 36 and the subsequent first directional rotation of the key causes the flange 68a to apply a force against the closest post 60a for movement of the lower carriage 35 upward to, in turn cause post 60b to lift lower cleat 31a from the tooth structure of the strap 12a. As a result of the first directional rotation of the key 68, the binding loop 12 is allowed to move in the first direction or the second direction, although upward movement may be prevented by the upper cleats and carriage, as will be described in detail below.

A second directional rotation of the key 68 causes the flange 68a to reduce force against the post for movement of the lower carriage 35 to engage the lower cleat 31a against the tooth structure of the binding loop 12. As a result of the second directional rotation of the key, the binding loop 12 is allowed to move in the first direction. Alternatively, the keyhole 36 may be positioned such that the insertion of the key into the keyhole 36 and the subsequent first directional rotation of the key 68 causes the flange 68a to apply a force against the post 60a for movement of the lower carriage 35 to engage the lower cleat 31a against the tooth structure of the binding loop 12. As a result of the first directional rotation of the key 68, the binding loop 12 is allowed to move in the first direction. Likewise, a second directional rotation of the key causes the flange 68a to reduce force against the post 60 for movement of the lower carriage 35 to disengage the lower cleat 31a from the tooth structure of the binding loop 12. As a result of the second directional rotation of the key, the binding loop 12 is allowed to move in either the first direction or second direction. It should be understood that concurrently, right lower cleat 31b is similarly controlled on the opposing side of the carriage 35. It should also be noted that the reverse side of the locking mechanism may include another key hole, such as 70 in FIG. 5 so that a key 68 may be used to manipulate lower carriage 35 from the opposite side of the apparatus 10.

Now turning to FIGS. 3-6, the locking mechanism 20 consists of at upper cleats 41a and 41b for controlling the movement of the binding loop strap material 12 through the groove 22. The upper cleats 41a, 41b are pivotally mounted to the locking mechanism 20 via pivot points 72, for engaging the tooth structure 12c of the binding loop strap material 12. The upper cleats 41a, 41b engage the tooth structure 12c of the binding loop 12 to ratchet the movement of the binding loop 12 in the second direction. The ratchet engagement of the upper cleats 41a, 41b permits the binding loop 12 to loosen until a dimension of the binding loop 12 is reached by the user.

Alternatively, upper cleats 41a, 41b may contain various configurations. For instance, the upper cleats 41a, 41b may employ more than one upper cleat to control the movement of the binding loop 12 for a stronger ratcheting mechanism. In addition, the upper cleats 41a, 41b may contain a tooth structure or other surfaces, such as an abrasive or non-smooth surface, for engaging the binding loop 12. As seen in FIG. 3, in similar fashion to cleats 31a, 31b, the upper cleats 41a, 41b have teeth on their free ends that engage with the ratchet teeth 12c on the straps 12a, 12b. However, upper cleats 41a, 41b control movement of the straps 12a, 12b in the opposite direction as the lower cleats 31a, 13b.

Figure 8:
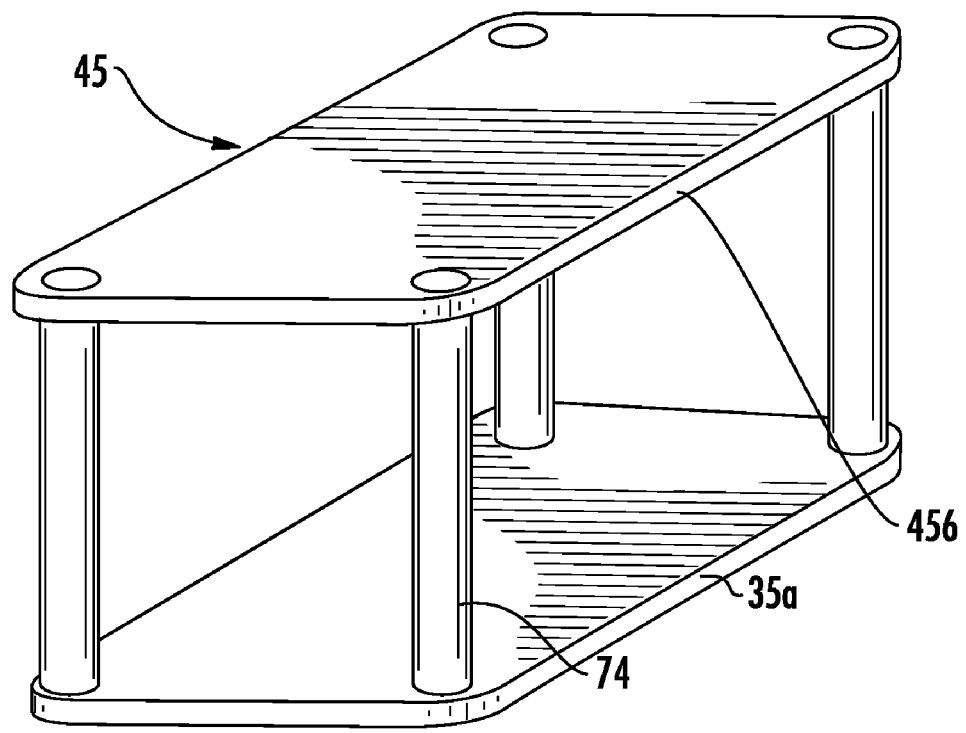
FIG. 8 is a perspective view of the upper carriage.

The upper cleats 41a, 41b, cooperate with upper carriage 45 for slideable adjustable control of the movement the upper cleats 41a, 41b. As seen in FIG. 8, the upper carriage 45 has two or more plates 45a, 45b, preferably metal, with four posts 74 in each for the corners to communicate with the upper cleats 41a, 41b. In one embodiment, corresponding seats 76a, 76b may be provided on the post engaging surfaces of the upper cleats 41a, 41b to receive the bottom posts 74 of the upper carriage 45 to achieve a lock position for disengagement of the cleats 41a, 41b from the strap 12 to permit movement therethrough. Releasing of the upper cleats 41a, 41b from the straps 12a, 12b upper carriage 45 permits the size of the binding loop 12 to be decreased. When the upper carriage positioned upwardly, the cleats 41a, 41a engage with the teeth 12c of strap 12 to prevent further tightening.

The upper carriage 45 may contain various configurations. For instance, the upper carriage 45 may employ more than or less than two plates 45a, 46b to engage with the upper cleats 41a, 41b. In addition, the upper carriage 45 may employ more than or less than four posts 74 to communicate with the upper cleats 41a, 41b. Also, the upper carriage 45 may slide in a variety of directions including horizontal or vertical slideable adjustment.

The upper carriage 45 may include a slide button 46, which protrudes through the locking mechanism 20 and housing 11. The slide button 46 is mounted to the upper carriage 45 for controlling the movement of the upper carriage 45. The slide button 46 being positioned such that downward movement of the slide button 46 causes downward movement of the upper carriage 45 to disengage the upper cleats 41a, 41b from the tooth structure 12c of the binding loop 12. As a result of the downward movement of the upper carriage 45, the binding loop 12 is allowed to move in the first direction or the second direction. With the key 68 not engaged with the lower carriage 35, only upward movement of the straps 12a, 12b will be possible thereby only permitting the loops 12 to become smaller. The upward movement of the slide button 45 causes upward movement of the upper carriage 45 to engage the upper cleats 41a, 41b against the tooth structure 12c of the binding loop 12. As a result of the upward movement of the upper carriage 45, the binding loop 12 will not be permitted to get any smaller.

Figure 6:
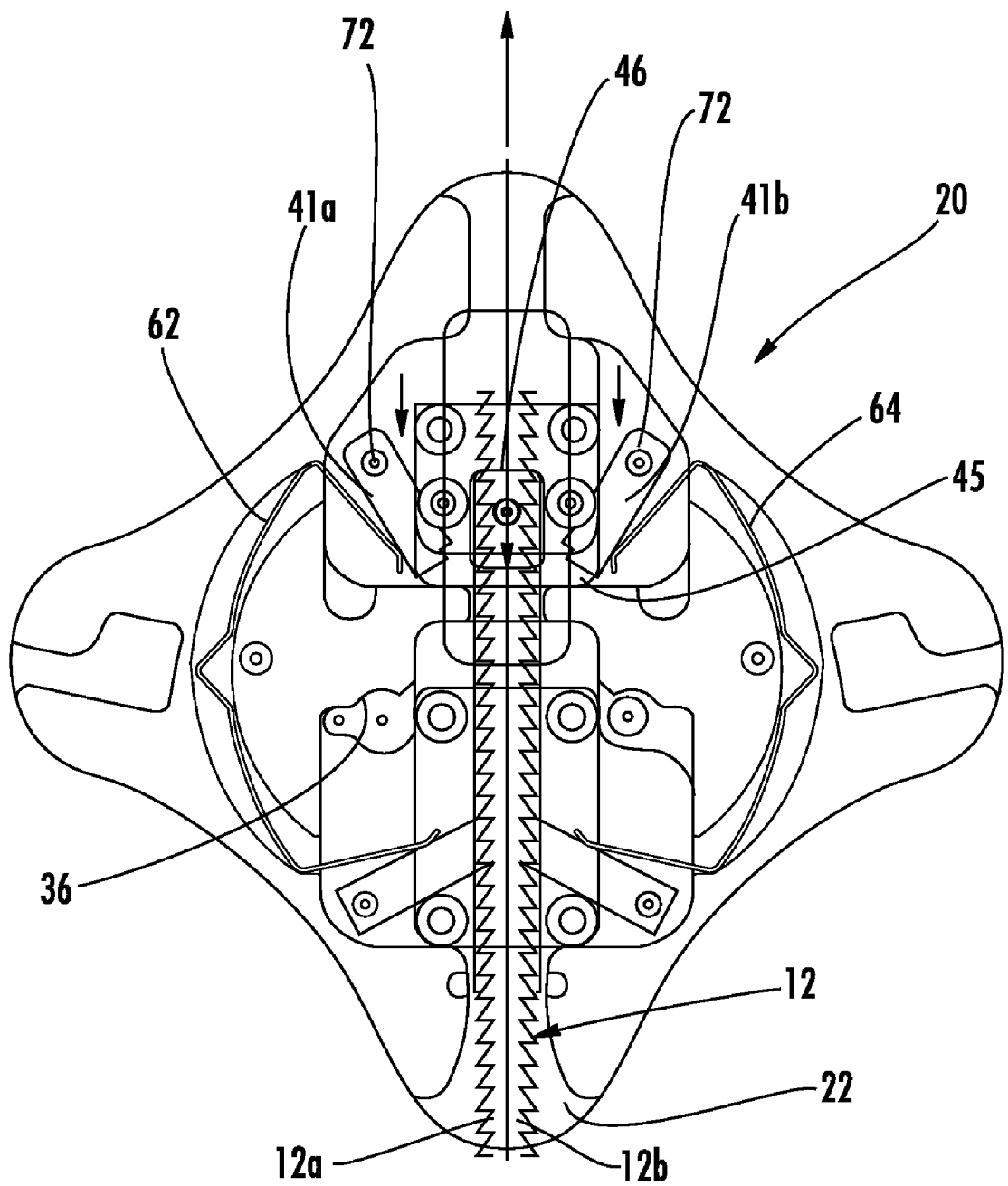
FIG. 6 is a cross-sectional view through the locking mechanism of FIG. 2 with slide lock engaged to permit tightening of the strap.

Still referring to FIG. 6, springs 62, 64 spring-biases the upper cleats 41a, 41b and upper carriage 45 upwardly for efficient and smooth ratcheting. This spring biasing is similar to the spring-biasing of lower cleats 31a, 31b and lower carriage 35.

In operation, the interior of the rigid housing 11 contains the locking mechanism 20 that controls movement of the binding loop 12, including individual straps 12a, 12b, through the groove 22. The locking mechanism 20 consists of the lower carriage 35 and the upper carriage 45 for controlling the movement of the lower cleats 31a, 31b and upper cleats 41a, 41b respectively. When the lower cleats 31a, 31b are engaged to the binding loop 12, the lower cleats 31a, 31b allow for the movement of the binding loop 12 in the first direction to permit sizing of the loop 12 smaller.

When the upper cleats 41a, 41b are engaged to the binding loop 12, the upper cleat 41 may allow for the movement of the binding loop 12 in the second direction, namely to permit the loop 12 to become large. The overall dimension of the binding loop 12 reduces when the binding loop 12 moves in the first direction. The overall dimension of the binding loop 12 increases when the binding loop 12 moves in the second direction. When both the lower cleats 31a, 31a and the upper cleats 41a, 41b are engaged, the overall dimension of the binding loop 12 may neither increase nor decrease.

When disengaged the lower cleats 31a, 31b are disengaged, movement of the binding loop 12 is possible in either the first direction or the second direction. When the upper cleats 41a, 41b are disengaged, movement of binding loop in either the first direction or the second direction is possible. Therefore, when the lower cleats 31a, 31b are disengaged and the upper cleats 41a, 41b is disengaged, the overall dimension of the binding loop 12 may increase or decrease freely when the binding loop 12 moves in the first or second direction.

Further, when disengaged, the lower cleats 31a, 31b may allow for the movement of the binding loop 12 in either the first direction or second direction. When engaged, the upper cleats 41a, 41b allow for the movement of binding loop 12 in the second direction. When the lower cleats 31a, 31b are disengaged and the upper cleats 41a, 41b are engaged, the overall dimension of the binding loop 12 can only increase when the binding loop 12 moves in the second direction.

Moreover, when engaged, the lower cleats 31a, 31b allow for the movement of the binding loop 12 in the first direction. When disengaged, the upper cleats 41a, 41b allow for the movement of binding loop 12 in the first direction or second direction. When the lower cleats 31a, 31b are engaged and the upper cleats 41a, 41b are disengaged, the overall dimension of the binding loop 12 can only decrease when the binding loop 12 moves in the first direction.

A holding device for the restraining apparatus 10 may be used to secure and house the apparatus 10 when not in use. For example, this holder or holster may be a flat box/container constructed of metal or plastic, for example, which measures 0.500 inch high×4.500-inch wide×8.00-inch deep. In addition, it has 0.500-inch flange on each side with screw holes for mounting. The holder is designed to contain the binding loop of the restraining apparatus while exposing the housing and the handle. This allows the user to pull the restraining apparatus by grasping the housing and pulling it from the enclosure without ratcheting or retracting the binding loops through the locking mechanism. The box/container may be mounted just below a vehicle's dashboard or anywhere on the door panel for easy access may be gained. It is also possible that the apparatus can be attached directly to the user, such as to their belt for easy access.

There are a number primary steps of a general method of deploying the restraining apparatus 10 to restrain an object. The user selects the restraining apparatus 10 including a binding loop of variable size. To release the binding loop 12 from its stored position, a slide button 46 is moved from its original location to move the upper carriage 45 and disengage the upper cleats 41a, 41b from the binding loop straps 12a, 12b. The binding loop 12 is now free to move in the first direction to decrease the overall dimension of the binding loop 12. To restrain an object, the binding loop 12 is placed around an object and the handle 13 is pulled, preferably with one hand, to move the binding loop 12 in the first direction until secure. Once the binding loop 12 is secure, the slide button 46 is returned to its original position to fix the position of the binding loop so that it cannot tighten further which may cause injury to the person being restrained. To provide a more comfortable fit, a standard cuff key 68 may be turned in a first directional rotation within the keyhole of the lower carriage 35. The lower carriage 35 thereby moves and subsequently disengages the lower cleats 31a, 31b which allows movement in the second direction to decrease the overall dimension of the binding loop 12. After a comfortable position is found, the standard cuff key 68 may be turned in a second directional rotation to move the lower carriage 35 back to its original position and thereby fix the position of the binding loop 12.

It would be appreciated by those skilled in the art that various changes and modifications can be made to the illustrated embodiments without departing from the spirit of the present invention. All such modifications and changes are intended to be covered by the appended claims.

What is claimed is:

1. A restraining apparatus for restraining an object, comprising:
    a housing defining a strap channel through an entire length of the housing, the housing defining a key aperture;
    a first and second strap each including teeth along a substantial surface of each strap, each strap, having a first end and a second end, configured to move through the entire length of the housing in unison in the same direction during movement through the strap channel; the first end of each strap being fixed inside the housing; the second end of each strap being slidably routed through an aperture defined in a bottom portion of the housing, through entire length of the housing, and exiting an aperture defined in a top portion of the housing; the first and second strap each being made of flexible material, whereby the first strap and second strap form a pair of loops capable of encircling two objects; the first and second straps being movable through the entire length of the housing in a first direction and a second direction;
    a single handle; the second end of the first and second strap both being connected to the single handle for pulling both the first and second strap in unison and in the same direction through the strap channel, the single handle being suitable for grasping by one hand of a user for one-handed operation;
    a first locking mechanism configured to prevent movement of the first and second straps in the first direction, the first locking mechanism including a first lower spring-biased locking cleat and a second lower spring-biased locking cleat engagable with teeth on the first and second straps, a lower carriage enclosing the first and second lower spring-biased cleats, the lower carriage engagable with the first lower spring-biased locking cleat and the second lower spring-biased locking cleat so the first lower spring-biased locking cleat and the second lower spring-biased locking cleat operate in unison;
    a second locking mechanism configured to prevent movement of the first and second straps in the second direction, the second locking mechanism including a first upper spring biased locking cleat and a second upper spring-biased locking cleat engagable with the teeth on the first and second straps, an upper carriage enclosing the first and second upper spring-biased cleats, the upper carriage engagable with the first upper spring-biased locking cleat and the second upper spring-biased locking cleat so the first upper spring-biased locking cleat and the second upper spring-biased locking cleat operate in unison; and
    button connected to the upper carriage whereby movement of the button causes the movement of the upper carriage,
    whereby when the first locking mechanism is disengaged and the second locking mechanism is engaged, the size of the encircling loop is only permitted to increase, and whereby when the first locking mechanism is engaged and the second locking mechanism is disengaged, the size of the encircling loop is only permitted to decrease.

2. The restraining apparatus of claim 1, wherein the lower carriage includes at least two plates joined together by a means for joining the at least two plates together to provide a structure for receiving the lower first and second lower spring-biased cleats.

3. The restraining apparatus of claim 2, wherein the first and second lower spring-biased locking cleats and the lower carriage are spring-biased by a wire spring.

4. The restraining apparatus of claim 3, wherein the lower carriage contains a keyhole, the keyhole includes a key pin that receives a distal flange of a key, the key hole positioned such that movement of the key causes the movement of the lower carriage to manipulate the lower carriage.

5. The restraining apparatus of claim 1, wherein the upper carriage includes at least two plates joined together by a means for joining the at least plates together to provide a structure for receiving the upper first and second lower spring-biased cleats.

6. The restraining apparatus of claim 5, wherein the first and second upper spring-biased locking cleats and the upper carriage are spring-biased by a wire spring.

* * * * *